Figure 2:
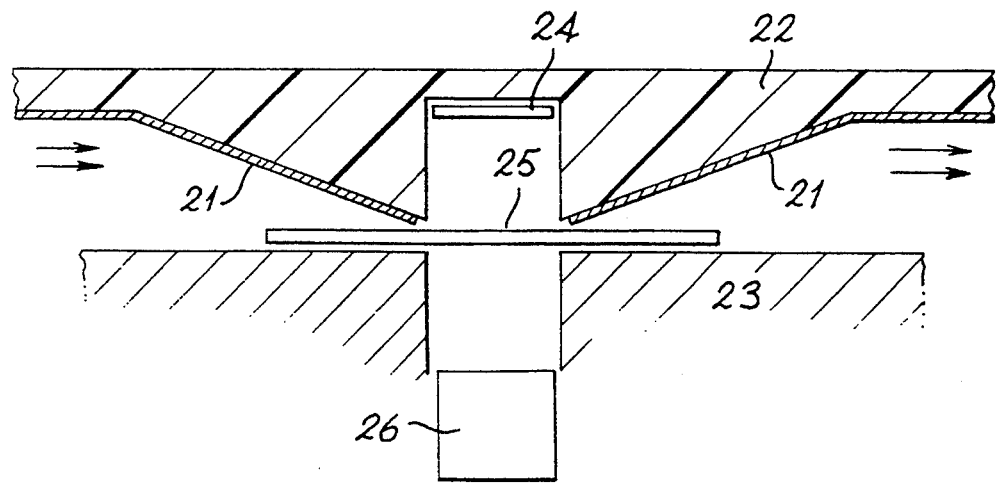

United States Patent [19]
Leck

[11] Patent Number: 5,442,190
[45] Date of Patent: Aug. 15, 1995

[54] METHOD AND APPARATUS FOR THE MEASUREMENT OF AIRBORNE FIBRES

[75] Inventor: Michael J. Leck, Goostrey, England

[73] Assignee: British Technology Group Ltd., London, England

[21] Appl. No.: 137,044

[22] PCT Filed: Apr. 16, 1992

[86] PCT No.: PCT/GB92/00700
§ 371 Date: Mar. 14, 1994
§ 102(e) Date: Mar. 14, 1994

[87] PCT Pub. No.: WO92/18842
PCT Pub. Date: Oct. 29, 1992

[30] Foreign Application Priority Data

Apr. 19, 1991 [GB] United Kingdom ............ 9108442.6

[51] Int. Cl.⁶ ............................................ G01N 15/06
[52] U.S. Cl. .................................. 250/573; 356/338
[58] Field of Search ................. 250/564, 573–576; 356/337–342, 441, 442; 340/627

[56] References Cited

U.S. PATENT DOCUMENTS 2,909,960 10/1959 Orr, Jr. et al. .................... 356/340
4,166,703 9/1979 Kirsch et al. ...................... 250/573
4,916,325 4/1990 Rood et al. ........................ 250/573

Primary Examiner—Stephone B. Allen
Attorney, Agent, or Firm—Cushman, Darby & Cushman

[57] ABSTRACT

Apparatus for measuring the quantity of fibers present in a gaseous fluid includes a pair of sloping shield electrodes (21) to shield charged fibers from the influence of a precipitating field other than in the region adjacent an optical detector (26).

6 Claims, 2 Drawing Sheets

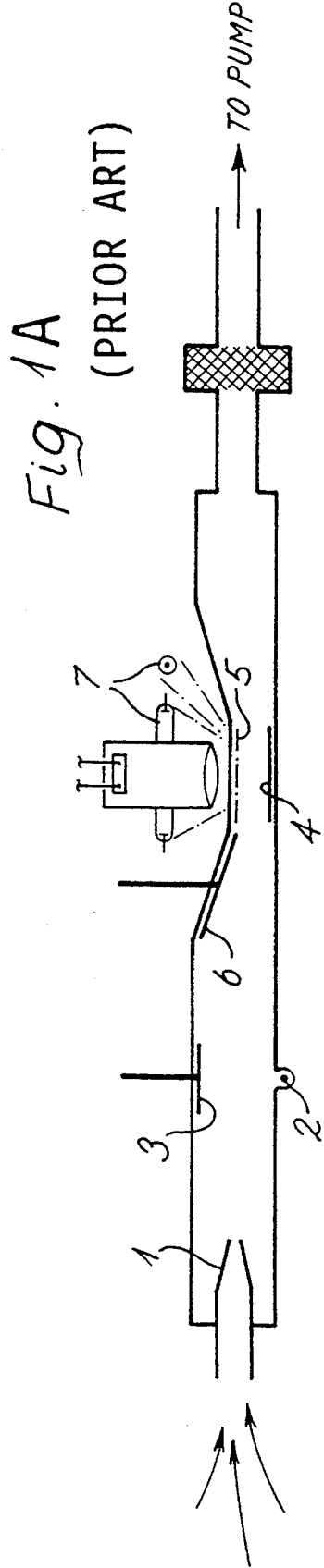
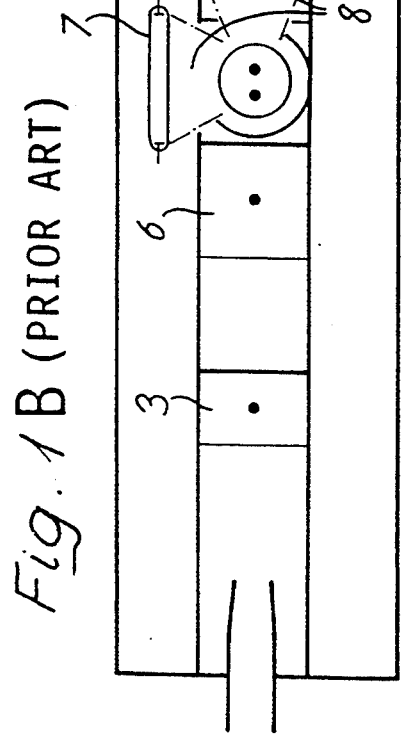
Fig. 1A (PRIOR ART)
Fig. 1B (PRIOR ART)
Fig. 1C (PRIOR ART)

METHOD AND APPARATUS FOR THE MEASUREMENT OF AIRBORNE FIBRES

This invention relates to the measurement of airborne fibres and, in particular to apparatus suitable for the measurement of the level of asbestos fibres in the air.

Some fibrous dusts present a hazard to man when inhaled as they have been shown to be human carcinogens. Asbestos fibres are the best Known example, and are controlled in the workplace by filtering a Known volume of air, and examining the sample under phase contrast optical microscopy. By counting fibres, a concentration in the original air can be determined.

There is a need for a cheap portable instrument that directly indicates the levels of fibres without the need to wait for a filter sample and microscope examination. Leak testing during the stripping of fibrous insulation is an example. To that end an approach to fibrous aerosol monitoring was made by combining the electrostatic precipitation of aligned fibres with differential light scattering along and at right angles to the fibre axis.

A prototype instrument has been constructed based on a parallel-plate precipitator with inertial fibre alignment. Fibre detection is based on a difference circuit which measures the scattered light from two low powered flash-lamps. The instrument is calibrated to read in fibres per ml of air sampled.

This instrument provides apparatus for measuring the quantity of fibres present in a gaseous fluid comprising means for creating of flow of said gaseous fluid through a chamber, aligning means to align the orientation of fibrous particles flowing into said chamber, electrical charging means to charge said particles within said chamber, electrical precipitating means to precipitate said fibrous particles on to carrier means, illuminating means to illuminate said carrier means with radiation and measuring means to measure radiation transmitted from said carrier means, thereby to derive an indication of the number of said particles precipitated thereon.

The disadvantage of this is that the precipitated deposit occurs over the whole length of the slide. Since the detection of fibres relies on analysing the light scatter, it would be advantageous if the precipitated deposit could be concentrated into this area. This can be achieved by using a modified flow channel and electrode.

According to the present invention there is provided apparatus for measuring the quantity of fibres present in a gaseous fluid comprising means for creating of flow of said gaseous fluid through a chamber, aligning means to align the orientation of fibrous particles flowing into said chamber, electrical charging means to charge said particles within said chamber, electrical precipitating means to precipitate said fibrous particles on to carrier means, illuminating means to illuminate said carrier means with radiation, measuring means to measure radiation transmitted from said carrier means and electrical screening means to shield said particles from the influence of said electrical precipitating means in regions not adjacent said measuring means, thereby to derive an indication of the number of said particles precipitated thereon.

Figure 3:
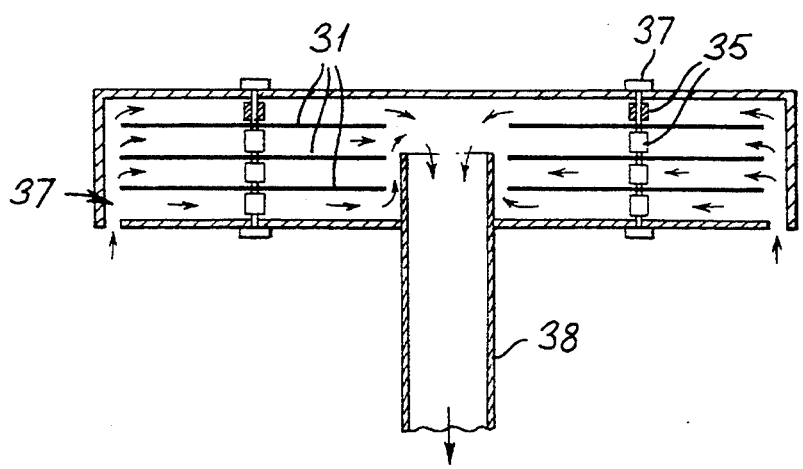

An embodiment of the invention will now be described by way of example, with reference to the accompanying drawings in which:

FIGS. 1A and 1B respectively show in elevation and plan a diagrammatic representation of our earlier portable airborne fibre monitor, FIG. 1C shows a plan view of the microscope cover slip of FIG. 1A FIG. 2 shows in elevation a modified fibre monitor in accordance with the present invention, and FIG. 3 is a schematic diagram of an elutriator suitable for use with the monitor of FIG. 2.

Referring now to the drawings, a pump draws air containing fibres into a slotted inlet nozzle 1 of the instrument where they are aligned by inertia. These aligned fibres are then charged by a corona discharge existing between a wire 2 and a first plate electrode 3. The charged fibres are then precipitated on to a microscope cover slip 4 beneath a conducting glass window 5 connected to a second plate electrode 6 which serves to precipitate the fibres. The electrical potentials on the corona and precipitating electrodes can be varied for each fibre type, but are typically 3,000 and 300 volts. Fibres are precipitated on to the cover slip retaining their axial alignment.

The number of fibres is directly related to the light scattering along and across the cover slip, and may be determined accurately by using high stability flash lamps 7, collimated by wedged light pipes 8, along and at right angles to the flow. The difference between alternate pulses is recorded using a single detector 9.

U.S. Pat. No. 4,916,325 describes a method of precipitating electrically charged fibres on to a microscope slide using a single precipitator (or repeller) electrode). The disadvantage of this is that the precipitated deposit occurs over the whole length of the slide. Since the detection of fibres relies on analysing the light scatter, it would be advantageous if the precipitated deposit could be concentrated into this area. This can be achieved by using a shaped flow channel and the revised electrode scheme illustrated in FIG. 2.

Referring now to FIG. 2, the electric field due to the precipitator electrode is screened from the charged fibres by the two sloping shield electrodes 21, mounted on an insulating body 22, which are held at the same potential (normally ground) as a conducting base plate 23. The fibres therefore move through a field free region and are not deposited until they are exposed to the field from a precipitator electrode 24. The deposition is thus constrained to occur in the small area 25 adjacent a light source and detectors 26. Since the fibres have been forced to move close to the slide surface in this region by the sloping shield electrodes the precipitation efficiency is high and fibre orientation is not significantly disturbed by high precipitator fields. In addition the flow velocity gradient experienced by the fibres as they reach the precipitation region also serves further to align them.

Preferably, overload of the fibre monitor slide by coarse, non-respirable dusts is minimised by some form of elutriation. A parallel plate elutriator, working by gravitational settling have been used for this s purpose. However, its sampling characteristic is not omnidirectional and, because its plates need to be sealed along the edges, it is difficult to clean.

We have found that a circular elutriator (FIG. 3) has none of these disadvantages. Such an elutriator, comprising annular discs 31 held by clamping screws and spacers 33,35 with a circumferential inlet passage 37 and central outlet passage 38. Since neither the top, bottom or plates have seals along their edges, they are easily removed for cleaning.

I claim:

1. Apparatus for measuring the quantity of fibres present in a gaseous fluid comprising means (1) for creating a flow of said gaseous fluid through a chamber, aligning means to align the orientation of fibrous particles flowing into said chamber, electrical charging means (3) to charge said particles within said chamber, electrical precipitating means (24) to precipitate said fibrous particles on to carrier means (25), illuminating means (7) to illuminate said carrier means with radiation, measuring means (26) to measure radiation transmitted from said carrier means characterised in that electrical screening means (21) are provided to shield said particles from the influence of said electrical precipitating means in regions not adjacent said measuring means.

2. Apparatus for measuring the quantity of fibres present in a gaseous fluid as claimed in claim 1 characterised in that it includes deflector means (21) positioned to increase the flow velocity of the gaseous fluid in the region of precipitation.

3. Apparatus for measuring the quantity of fibres present in a gaseous fluid as claimed in claim 2 characterised in that said deflector means comprises a pair of two sloping shield electrodes (21).

4. Apparatus for measuring the quantity of fibres present in a gaseous fluid as claimed in claim 1 characterised in that elutriator means (31, 73, 39) are provided to reduce the amount of coarse non-respirable particles carried by said gaseous fluid.

5. Apparatus for measuring the quantity of fibres present in a gaseous fluid as claimed in claim 4 characterised in that said elutriator means comprises at least a pair of spaced annular discs (31) having a circumferential inlet passage (37) and central outlet passage (39).

6. Apparatus for measuring the quantity of fibres present in a gaseous fluid as claimed in claim 4 characterised in that said annular discs (31) are demountable for cleaning purposes.

* * * * *